United States Patent [19]

Krampe et al.

[11] Patent Number: 4,693,776

[45] Date of Patent: Sep. 15, 1987

[54] MACROMER REINFORCED PRESSURE SENSITIVE SKIN ADHESIVE

[75] Inventors: Stephen E. Krampe; Cheryl L. Moore; Charles W. Taylor, all of St. Paul, Minn.

[73] Assignee: Minnesota Mining and Manufacturing Company, St. Paul, Minn.

[21] Appl. No.: 797,851

[22] Filed: Nov. 14, 1985

Related U.S. Application Data

[63] Continuation-in-part of Ser. No. 734,907, May 16, 1985, abandoned.

[51] Int. Cl.[4] ............................................. C09J 5/00
[52] U.S. Cl. ...................................... 156/327; 128/156; 156/331.5; 156/332; 424/448; 427/208.4; 428/355; 428/356; 523/111; 525/227
[58] Field of Search ............... 156/327, 332, 331.5; 523/111; 427/208.4; 525/227; 424/28; 428/355, 356; 128/156

[56] References Cited

U.S. PATENT DOCUMENTS

| | | | |
|---|---|---|---|
| Re. 24,906 | 12/1960 | Ulrich | 206/59 |
| 2,884,126 | 4/1959 | Ulrich | 206/59 |
| 3,004,958 | 10/1961 | Berens | 260/86.3 |
| 3,121,021 | 2/1964 | Copeland | 117/122 |
| 3,135,717 | 6/1964 | Gregorian | 260/45.5 |
| 3,321,451 | 5/1967 | Gander | 260/79.3 |
| 3,475,363 | 10/1969 | Gander | 260/29.7 |
| 3,532,652 | 10/1970 | Zang et al. | 260/23 |
| 3,725,122 | 4/1973 | Reinhard et al. | 428/355 |
| 3,786,116 | 1/1974 | Milkovich | 260/885 |
| 3,832,423 | 8/1974 | Milkovich | 260/878 |
| 3,862,267 | 1/1975 | Milkovich | 260/878 |
| 4,007,311 | 2/1977 | Harlan | 428/246 |
| 4,075,186 | 2/1978 | Ambrose et al. | 260/887 |
| 4,140,115 | 2/1979 | Schonfeld | 128/156 |
| 4,260,659 | 4/1981 | Gobran | 428/217 |
| 4,323,557 | 4/1982 | Rosso et al. | 424/28 |
| 4,374,883 | 2/1983 | Winslow | 428/40 |
| 4,551,388 | 11/1985 | Schlademan | 428/355 |
| 4,554,324 | 11/1985 | Husman et al. | 525/301 |

FOREIGN PATENT DOCUMENTS

872532  7/1961  United Kingdom .

*Primary Examiner*—John J. Gallagher
*Attorney, Agent, or Firm*—Donald M. Sell; James A. Smith; Dale E. Hulse

[57] ABSTRACT

A skin adhesive coated sheet material is provided which is coated with a polymer that exhibits an enhanced level of initial adhesion when applied to skin but resists objectionable adhesion build up over time. The skin adhesives are comprised of a macromer reinforced acrylate copolymer which has a creep compliance value at least about $1.2 \times 10^{-5}$ cm$^2$/dyne.

19 Claims, No Drawings

MACROMER REINFORCED PRESSURE SENSITIVE SKIN ADHESIVE

RELATED APPLICATIONS

This application is a continuation-in-part of application Serial No. 734,907, filed May 16, 1985, now abandoned.

FIELD OF THE INVENTION

This invention relates to a skin adhesive composition and to a tape utilizing such an adhesive. More particularly, the invention relates to a skin adhesive comprised of an acrylate copolymer having an enhanced level of initial adhesion to skin and resistance to objectionable adhesion build over time. This invention also relates to a stable chemical complex of iodine, iodide and the skin adhesive described above.

BACKGROUND OF THE INVENTION

Pressure sensitive adhesive tapes have been used for more than half a century for a variety of marking, holding, protecting, sealing and masking purposes. The earliest medical applications where the product was referred to as an adhesive plaster were not pressure sensitive adhesives. These were, in fact, crude mixtures of natural rubber plasticized and tackified with wood rosin derivatives and turpentine and heavily pigmented with zinc oxide. These tape-like products served their purpose but, with the advent of the truly pressure sensitive adhesives, they were replaced. The term PSA has a very precise technical definition and has been dealt with extensively in the technical literature, examples of which are Chapter 17 of Houwink and Salomon "Adhesion and Adhesives", Vol. 2, Elsevier Publishing Company, 1967, and the "Handbook of Pressure-Sensitive Technology" edited by Donatas Satas, published by Van Nostrand Reinhold Company, 1982.

Fundamentally, PSA's require a delicate balance of viscous and elastic properties which result in a four-fold balance of adhesion, cohesion, stretchiness and elasticity. In essence, PSA products have sufficient cohesiveness and elasticity so that, despite their aggressive tackiness, they can be handled with the fingers and removed from smooth surfaces without leaving residue. General trade usage does not sanction the extension of the term PSA to embrace tapes and adhesives merely because they are "sticky" or because they adhere to a particular type of surface.

The prior art relating to graft copolymers is directed to modifying systems for the purpose of imparting flexibility to rigid or semi-rigid polymeric backbones. The patents of Behrens (U.S. Pat. No. 3,004,958), Gregorian (U.S. Pat. No. 3,135,717), and Milkovich (U.S. Pat. Nos. 3,786,116; 3,832,423; 3,862,267) teach how to graft side chains of polystyrene or acrylate esters onto rigid or semi-rigid backbones of polyvinyl chloride or methacrylate esters to provide flexibility and temperature and impact resistance. Block copolymers of the styrene-isoprene-styrene type have had their adhesion enhanced by grafting of methyl methacrylate as taught by Harlan (U.S. Pat. No. 4,007,311). This was done without regard for elasticity or cohesiveness. In Ambrose (U.S. Pat. No. 4,075,186), a butadiene side chain is grafted to an acrylate polymer backbone to produce a molded product which has improved impact resistance but which is tack-free. British Pat. No. 872,532 is a process patent which deals fundamentally with the preparation of graft copolymers and clearly demonstrates the advantages of grafting using different methods of grafting polystyrene onto polymethacrylate.

U.S. Application Ser. No. 419,025 filed Sept. 16, 1982, still pending, discloses macromer reinforced copolymers for use as pressure-sensitive adhesives. A division of application Ser. No. 419,025 was filed on Apr. 4, 1985 and was assigned Ser. No. 719,794; That patent discloses that the use of a macromer to reinforce the copolymer allows for a substantial increase in the shear strength of the copolymer. The examples are limited to application of the adhesive to relatively non-conformable backings, e.g., polyethylene terephthalate.

The difficulty of adhering tape or other devices to the human skin has long been recognized. The irregular and complex surface of the skin presents obstacles in itself and the wide variation in the skin surface from individual to individual and from site to site compound these obstacles. Acrylic PSAs have been used for many years in medical and surgical applications. An outstanding acrylic copolymer, of the type described in U.S. Pat. No. 2,884,126/RE 24,906 (Ulrich) has been employed in a porous, surgical adhesive tape, U.S. Pat. No. 3,121,021 (Copeland) with very acceptable skin adhesion performance. The desirable features of an acrylic PSA in medical applications, such as less irritation to the skin, were recognized in U.S. Pat. No. 3,321,451 (Gander), as well as the disadvantages which result from adhesion buildup when the acrylic PSA is in contact with the skin for long periods of time. According to this patent, the irritation caused by removal of the tape was overcome by including in the acrylate adhesive polymer certain amine salts which made it possible to remove the tape by washing with water which is not always feasible where high standards of sterility are being maintained.

In Gander U.S. Pat. No. 3,475,363), the inventor has attempted to overcome the objectionable compliance failure in the acrylate PSA by employing as a crosslinking agent dimethylaminoethyl methacrylate to ensure adhesion to the skin without deleterious effects. Zang (U.S. Pat. No. 3,532,652) recognizes that acrylate PSAs suffer when used on surfaces which promote migration of oils and the like to the adhesive, thereby weakening their cohesive strength. Zang overcomes this by partially crosslinking his acrylate interpolymer with polyisocyanate. In Schonfeld (U.S. Pat. No. 4,140,115), the inventor reduces the stripping of tissue cells when his acrylate PSA is removed from the skin by blending the PSA with an unreacted polyol having a fatty acid ester pendant moiety. This adhesive has a tendency to leave objectionable residue.

Another approach to modifying PSA tape for the purpose of controlling the degree of elastic compliance and viscous flow can be found in Gobran (U.S. Pat. No. 4,260,659) which relies upon and teaches how a plurality of superimposed adhesive layers having different gradients of shear creep compliance can meet the requirement of releasable adhesion to a plastic surface such as polyethylene. In Winslow (U.S. Pat. No. 4,374,883) the shear creep compliance is achieved and the cohesive strength maintained by combining two layers of adhesive which reinforce each other. While both of these address the problem of modifying a PSA to improve compliance, neither deals with the kind of precision and control required in medical products which are adhered to the skin.

U.S. Pat. No. 4,323,557 discloses a stable chemical complex of iodine, iodide and a dermatologically acceptable room temperature tacky pressure-sensitive adhesive which is substantially free of acidic components.

SUMMARY OF THE INVENTION

This invention relates to a skin adhesive coated sheet material comprising a conformable backing member and a coating covering at least a portion of one major surface thereof of a polymer having in its backbone a polymerized monomeric acylate or methacrylate ester of a non-tertiary alcohol, said alcohol having from 1 to 14 carbon atoms with the average number of carbon atoms being about 4 to 12, and having attached to said backbone, polymeric moieties having a weight average molecular weight above about 2,000 and a $T_g$ above about 20° C.; wherein the number and composition of the polymeric moieties in said polymer and the inherent viscosity of said polymer are such as to provide said adhesive composition with a creep compliance value of at least about $1.2 \times 10^{-5}$ cm$^2$/dyne.

More particularly, this invention relates to a skin adhesive coated sheet material having an adhesive comprising a copolymer consisting essentially of copolymerized repeating A monomers, C macromers, and, optionally, B monomers, wherein:

A is a monomeric acrylate or methacrylate ester of a non-tertiary alcohol, said alcohol having from 1 to 14 carbon atoms with the average number of carbon atoms being about 4–12;

B, when used, is at least one ethylenically-unsaturated compound copolymerizable with said monomeric acrylate ester, the amount by weight of B monomer being up to 25% of the total weight of all monomers; and C is a macromer having the general formula: $X-(Y)_n-Z$ wherein x is a vinyl group copolymerizable with said A and B monomers; Y is a divalent linking group; where n can be zero or 1; and Z is a monovalent polymeric moiety having a $T_g$ greater than about 20° C. and a molecular weight in the range of about 2,000 to about 30,000 and being essentially unreactive under copolymerization conditions; wherein said vinyl group and said A and B monomers form a polymeric backbone having pendant therefrom said polymeric moieties and wherein the weight of said C macromer and the inherent viscosity of the copolymer are such that the adhesive composition has a creep compliance value of at least about $1.2 \times 10^{-5}$ cm$^2$/dyne.

The skin adhesive coated sheet is preferably in the form of a tape or dressing which can be applied to this skin to yield an enhanced level of initial adhesion to the skin without objectionable adhesion build over time.

This invention also relates to a method of adhering a substrate to skin comprising interposing between said substrate and skin an effective amount of the skin adhesive described above.

In the present invention, the PSA has been chemically tailored to produce within physically defined parameters a skin adhesive for a tape which is a significant advance over the prior art in its ability to conform to the human skin surface and be removed after a resonable period of time without undue irritation to the skin and without leaving objectionable residue. The optimization of these two porperties without upsetting the delicate four-fold balance of adhesion, cohesion, stretchiness and elasticity has required a unique combination of polymerization techniques which control the rheological properties which contribute to the bond-making (compliance) and the bond-breaking (release) properties of a PSA coated material which has been in moderately long contact with the human skin.

This invention also relates to a stable chemical complex of iodine, iodide and a pressure-sensitive adhesive comprised of a polymerized monomeric acrylate or methacylate ester of a non-tertiary alcohol, said alcohol having from 1 to 14 carbon atoms with the average number of carbon atoms being about 4 to 12, and having attached to said backbone polymeric moieties having a weight average molecular weight above about 2,000 and a Tg above about 20° C.; wherein the number and composition of the polymeric moieties in said polymer and the inherent viscosity of said polymer are such as to provide said ahesive composition with a creep compliance value of at least about $1.2 \times 10^{-5}$ cm$^2$/dyne.

DETAILED DESCRIPTION OF THE INVENTION

In accordance with the invention, a skin adhesive comprises a polymer having in its backbone at least a major portion by weight of polymerized monomeric acrylic or methacrylic acid ester of a non-tertiary alcohol having from 1 to 14 carbon atoms with the average number of carbon atoms being 4–12 and grafted to the backbone polymeric moieties having a $T_g$ greater than about 20° C. and a weight average molecular weight above about 2,000. The number and composition of the attached polymeric moieties in the polymer and the inherent viscosity of the polymer are such as to provide an adhesive composition with a creep compliance value of greater than $1.2 \times 10^{-5}$ cm$^2$/dyne.

Preferably the skin adhesive composition comprises a copolymer which consists essentially of copolymerized repeating units from A monomers and C macromers and optionally B monomers. A is a monomeric acrylic or methacrylic acid ester of a non-tertiary alcohol, said alcohol having from 1 to 14 carbon atoms with the average number of carbon atoms being about 4–12. When used, B is at least one ethylenically unsaturated compound copolymerizable with the monomeric acrylic acid ester. B monomers generally reduce the flexibility of the copolymer. Preferred B monomers are acrylic acid, methacrylic acid, itaconic acid, acrylamide, methacrylamide, acrylonitrile, methacrylonitrile, vinyl acetate and N-vinylpyrrolidone. C is a macromer having the general formula $X-(Y)_n-Z$ wherein X is a vinyl group copolymerizable with the A and B monomers. Y is a divalent linking group where n can be zero or one. Z is a monovalent polymeric moiety having a $T_g$ greater than 20° C. and a weight average molecular weight in the range of about 2,000 to 30,000 preferably 4,000 to 20,000 and being essentially unreactive under copolymerization conditions. The vinyl group of the C macromer and the A and B monomers are copolymerized to form a backbone having pendant therefrom the polymeric moieties.

The number and composition of C macromers and the inherent viscosity of the polymer are adjusted to obtain the desired degree of creep compliance. For a polymer of given flexibility, i.e. a given A and B composition, an increase in the amount of C macromer will decrease the level of creep compliance of the polymer. Likewise, an increase in the inherent viscosity of the copolymer adhesive will decrease the level of creep compliance. Accordingly as the amount of C macromer is increased, the inherent viscosity of the copolymer adhesive should be decreased to obtain a comparable level of creep compliance. For example, a preferred composition of the copolymer adhesive is 96 parts iso-octyl acrylate, 2 parts acrylic acid and 2 parts of a polystyrene macromer having a molecular weight of about 8,000 to about 15,000. For this particular composition, the inherent viscosity of the resulting copolymer should be from about 0.85 to about 0.95. If the amount of C macromer is decreased, the inherent viscosity of the copolymer adhesive should be increased to obtain comparable level of creep compliance and, likewise, if the amount of C macromer is increased the inherent viscosity should be decreased to obtain a comparable level of creep compliance.

In general, the inherent viscosity of the copolymer adhesive should range from about 0.5 to about 1.4, more preferably 0.55 to 1.1. The inherent viscosities (IV) reported herein were obtained by conventional methods used by those skilled in the art. The so-called IV's were obtained using a Cannon-Fenske 50 viscometer in a water bath controlled at 25° C. to measure the flow time of 10 ml of a polymer solution (0.2 g per deciliter polymer in ethyl acetate). The test procedure followed and the apparatus used are described in detail in "Textbook of Polymer Science", F. W. Billmeyer, Wiley-Interscience, Second Edition, 1971, Pages 84 and 85.

The weight of C macromer is generally within the range of about 1% to 30%, preferably 1% to 7%, of the total weight of all monomers in the copolymer.

Monomer A, as previously mentioned, is a monomeric acrylic or methacrylic acid ester of a non-tertiary alcohol, said alcohol having from 1 to 14 carbon atoms with the average number of carbon atoms being about 4-12. Examples of such monomers include the esters of acrylic acid or methacrylic acid with non-tertiary alkyl alcohols such as 1-butanol, 1-pentanol, 2-pentanol, 3-pentanol, 2-methyl-1-butanol, 1-methyl-1-butanol, 1-methyl-1-pentanol, 2-methyl-1-pentanol, 3-methyl-1-pentanol, 2-ethyl-1-butanol, 3,5,5-trimethyl-1-hexanol, 3-heptanol, 2-octanol, 1-decanol, 1-dodecanol, and the like. Such monomeric acrylic or methacrylic esters are known in the art and many are commerically available.

As mentioned above, the B monomer is an ethylenically unsaturated compound copolymerizable with the monomeric acrylic acid ester and is employed to modify the flexibility of the copolymer. In general, the addition of the B monomer reduces the flexibility of the copolymer. Preferred B monomers are acrylic acid, methacrylic acid, itaconic acid, acrylamide, methacrylamide, acrylonitrile, methacrylonitrile, vinyl acetate, and N-vinylpyrrolidone. The B monomer is not necessary to produce the skin adhesive, but up to 25% of the total weight of all monomers of B monomer may be included. The preferred skin adhesive according to the present invention will contain from about 1% to about 15% by weight of B monomer of the total weight of all monomers. In the preferred skin adhesive, the amount of acrylic acid or acrylamide will range from about 1% to about 4% by weight of total monomer. In skin adhesives containing N-vinylpyrrolidone as the B monomer, the preferred copolymer will contain from about 5% to about 15% of N-vinylpyrrolidone by weight of total monomers.

The C macromer is a polymeric material having a copolymerizable vinyl group with which the A monomer and the B monomer will copolymerize under the polymerization conditions. The C macromer is represented by the general formula $X-(Y)_n-Z$ wherein X is a vinyl group copolymerizable with the A and B monomers;

Y is a divalent linking group where n can be zero or one; and

Z is a monovalent polymeric moiety having a $T_g$ greater than 20° C. and a weight average molecular weight in the range of about 2,000 to 30,000 and being essentially unreactive under copolymerization conditions.

The preferred C macromer useful in the present invention may be further defined as having an X group which has the general formula

wherein R is a hydrogen atom or a COOH group and R' is a hydrogen atom or methyl group. The double bond between the carbon atoms provides a copolymerizable moiety capable of copolymerizing with the A and B monomers.

The preferred C macromer useful in preparing compositions according to the present inventon includes a Z group which has the general formula

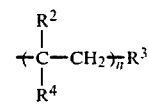

wherein $R^2$ is a hydrogen atom or a lower alkyl group, $R^3$ is a lower alkyl group, n is an integer from 20 to 500 and $R^4$ is a monovalent radical selected from the group consisting of

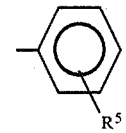

and $-CO_2R^6$ wherein $R^5$ is a hydrogen atom or a lower alkyl group and $R^6$ is a lower alkyl group.

Preferably, the C macromer has a general formula selected from the group consisting of

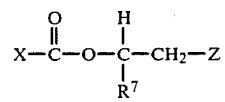

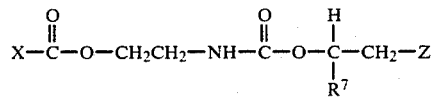

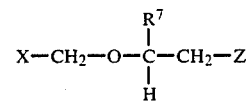

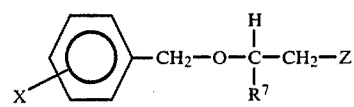

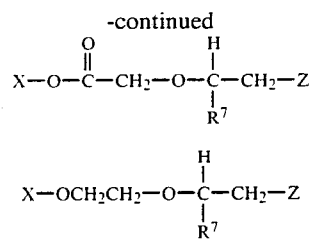

wherein $R^7$ is a hydrogen atom or a lower alkyl group.

The C macromer is a functionally terminated polymer having a single functional group (the vinyl group) and is sometimes identified as a "semitelechelic" polymer. (Vol. 27 "Functionally Terminal Polymers Via Anionic Methods" D. N. Schultz et al, pages 427-440, *Anionic Polymerization,* American Chemical Society [1981].) Such macromers are known and may be prepared by the method disclosed by Milkovich et al in U.S. Pat. Nos. 3,786,116 and 3,842,059, the disclosures of which are incorporated herein by reference for the description of the preparation of the vinyl-terminated macromers. (As disclosed therein, vinyl-terminated macromer is prepared by anionic polymerization of a polymerizable monomer to form a living polymer.) Such monomers include those having an olefinic group, such as the vinyl-containing compounds. Living polymers are conveniently prepared by contacting the monomer with an alkali metal hydrocarbon or alkoxide salt in the presence of an inert organic diluent which does not participate in or interfere with the polymerization process. Monomers which are susceptible to anionic polymerization are well known. Illustrative species include vinyl aromatic comounds such as styrene, alpha-methylstyrene, vinyltoluene and its isomers or non-aromatic vinyl compounds such as methyl methacrylate. Other monomers susceptible to anionic polymerization are also useful.

The initiators for anionic polymerization may be any of the alkali metal hydrocarbons or alkoxide salts which produce a mono-functional living polymer, i.e., only one end of the polymer contains a reactive ion. Such initiators include the hydrocarbons of lithium, sodium or potassium, for example, having an alkyl radical containing up to 20 carbon atoms or more, and preferably up to 8 carbon atoms. Illustrative alkali metal hydrocarbons include ethylsodium, propylsodium, butylpotassium, octylpotassium, phenylsodium, ethyllithium, butyllithium, sec-butyllithium, isobutyllithium, tert-butyllithium and 2-ethylhexyllithium. Sec-butyllithium is the preferred initiator.

The inert organic diluent utilized to facilitate heat transfer and adequate mixing of the initiator and monomer preferably is a hydrocarbon or an ether. Useful diluents include saturated aliphatic and cycloaliphatic hydrocarbons such as hexane, heptane, octane, cyclohexane and the like. In addition, aliphatic and cyclic ether solvents may be used, for example, dimethyl ether, diethyl ether, and tetrahydrofuran.

The amount of initiator usually dictates the molecular weight of the living polymer. If a small portion of initiator is used, with respect to the amount of monomer, the molecular weight of the living polymer will generally be larger than if the large portion of initiator is used. It is generally advisable to add initiator dropwise to the monomer until the persistence of the characteristic color of the organic anion is observed, then the calculated amount of the initiator is added for the molecular weight desired. The preliminary dropwise addition serves to destroy contaminants and thus permits better control of the polymerization. Generally, the initiator concentration can vary from about 0.01 to about 0.1 mole of active alkali metal per mole of monomer, or higher. Preferably, the concentration of the initiator will be from about 0.01 to about 0.04 mole of active alkali metal per mole of monomer.

The temperature of the polymerization will depend upon the monomer. Generally, the reaction can be carried out at a temperature ranging from about $-100°$ C. up to about 100° C.

The anionic polymerization must be carried out under controlled conditions so as to exclude substances which destroy the initiator or living anion. Water and oxygen must be excluded. The polymerization therefore is carried out under anhydrous conditions in an inert atmosphere such as nitrogen, helium or argon.

The living polymers may be terminated in several ways. It is important, however, that conditions be selected to provide a quantitative termination free from side reactions. Under certain conditions the living polymeric anion may be allowed to react directly with halogen-containing terminating agents to produce, for example, vinyl-terminated macromers. In many cases, however, the polymeric anion is highly reactive and non-selective in its reacion with the terminating agent. In addition to displacement of the halogen atom, it may abstract hydrogen atoms or react with other functional groups present, including the vinyl group itself. This results in polymer chains which are non-functional or of unwanted functionality and molecular weight. Occasionally, under these conditions, a vinyl-terminated polymer may be attacked by living anion and its functionality destroyed.

One means for overcoming the foregoing problem is to render the living anion less reactive, thus less susceptible to side reactions, by "capping" with a less reactive end group prior to actual termination. Examples of suitable "capping agents" include lower alkylene oxides such as ethylene and propylene oxide, and 1,1-diphenylethylene, etc. A preferred capping agent is an alkylene oxide, such as ethylene oxide. The capping agent reacts with the living polymer, destroying its oxirane ring. The alkoxide anion then displaces the halogen atom of the terminating agent selectively, leaving the vinyl group intact.

The capping reaction is carried out quite simply, as in the case of the terminating reaction, by adding the capping reactant to the living polymer at the polymerization temperature. The reaction occurs immediately. As in the case of the termination reaction, a slight molar excess of the capping reactant with respect to the amount of initiator may be used. The reaction occurs on a mole for mole basis. This reaction is described in Milkovich, U.S. Pat. No. 3,842,059. Reaction with the terminating agent provides the desired vinyl-terminated macromer.

A second method of termination, also useful for synthesis of the vinyl-terminated polymeric monomers, involves capping the living anion performed as described previously, and then protonating the alkoxide ion to produce a hydroxyl-terminated polymer. The hydroxyl group is then allowed to react with a terminating agent containing an isocyanate group (instead of a halogen atom) to produce the vinyl termination. Suitable terminating agents for this reaction are isocyanato alkyl acrylates and methacrylates having 1 to 4 carbon atoms in the alkyl group. The hydroxyl and isocyanato groups react to form a urethane linkage between the polymeric segment and the "monomeric" end group. Intermediate protonation of the alkoxide is necessary to prevent unwanted side reactions upon termination.

Although U.S. Pat. No. 3,786,116 teaches that the molecular weight distribution of the polymer chains of the vinyl-terminated macromer prior to copolymerization must be narrow, i.e., less than 1.1 polydispersity, it has been found that useful psa compositions according to the present invention may employ polymeric monomer having a polydispersity of up to about 3 without deleterious effects on the adhesive properties. These broader molecular weight distributions may be obtained by known variations in temperature of polymerization and the lithium alkali initiator used.

The vinyl-terminated macromers useful in the present invention may also be prepared by free-radical polymerization (rather than anionic polymerization). Known methods can be used to prepare semi-telechelic polymers using thermal free-radical initiators. An illustrative method is described in Y. Yamashita, K. Ito, H. Mizuno and H. Okada, Polymer Journal 14, 255-260 (1982) and K. Ito, N. Usami, and Y. Yamashita, Macromolecules 13, 216-221 (1980). These functional polymers can then be converted into vinyl-terminated monomers using standard condensation chemistry, ring opening reactions, etc. Specifically, carboxylic-acid terminated low molecular weight polystyrene can be prepared using 4,4'-azobis-(4-cyanovaleric acid) as an initiator and an acid-containing chain transfer agent such as HS—CH$_2$—COOH. The semi-telechelic polystyrene can then be vinyl terminated via, for example, ring opening of glycidyl methacrylate. These vinyl-terminated polymers have a high polydispersity.

The copolymerization of the A monomer, B monomer, if used, and C macromer is by conventional free radical polymerization, for example, as described by Ulrich, U.S. Re. Pat. No. 24,906. The monomers and macromers are dissolved in a suitable inert organic solvent and polymerized by standard free radical polymerization utilizing a suitable free radical initiator. Suitable free radical initiators which may be utilized include azo compounds such as 2,2'-azobis(isobutyronitrile), hydroperoxides such as tert-butyl hydroperoxide, peroxides such as benzoyl peroxide or cyclohexanone peroxide. Generally, from about 0.01 to about 5% by weight of thermally activatable initiator based upon the total polymerizable composition is used.

The organic solvent utilized in the latter free radical polymerization may be any organic liquid which is inert to the reactants and product and will not otherwise adversely affect the reaction. Suitable solvents include ethyl acetate and mixtures such as ethyl acetate with toluene, heptane with toluene and isopropyl alcohol and heptane with toluene and methyl alcohol. Other solvent systems are useful. The amount of solvent is generally about 30-80% by weight based on the total weight of the reactants and solvent. In addition to solution polymerization herein described, said copolymerization may be carried out by other well known techniques such as suspension, emulsion and bulk polymerization.

As described above, the preferred grafting technique involves copolymerization of monomer A, B (if used) and macromer C with C being a chemically tailored macromolecular monomer of controlled molecular weight and selected to have a $T_g$ sufficiently high to optimize the creep compliance of the compliant acrylic backbone. Other polymer grafting techniques may also be employed to produce the improved creep compliant skin adhesive compositions of the invention. Each of the grafting methods provides a high degree of predictability of the properties of the end product.

An alternative grafting technique involves preforming the compliant, acrylic polymeric backbone, then copolymerizing the preformed polymeric backbone with monomer to produce high $T_g$ polymeric moieties on the backbone to obtain the desired creep compliance. Such a composition may be obtained, for example, by grafting methyl methacrylate monomer to a preformed acrylic polymer backbone.

Another equally effective approach is to graft preformed high $T_g$ polymeric moieties to a preformed compliant acrylic backbone. Such a composition may be obtained, for example, by grafting hard hydroxy-terminated polystyrene moieties to a preformed acrylic polymer backbone.

These and other useful polymer grafting techniques are well known as described in overview in Chapter 2, pages 13-16 *Block Copolymers* by Noshay and McGrath, Academic Press (1977) and in greater detail in *Graft Copolymers*, Battaerd and Tregear, J. Wiley & Sons (1967).

When the B monomer chosen is one which will form a stable chemical complex with iodine, the skin adhesive can be given antimicrobial activity by the formation of a stable chemical complex of iodine, iodide and the skin adhesive. Suitable iodine complexing monomers include N-vinylpyrrolidone. U.S. Pat. No. 4,323,557, which is hereby incorporated herein by reference thereto, generally discloses the process of forming a stable chemical complex of iodine, iodide and a pressure-sensitive adhesive without regard to the creep compliance of the adhesive.

The process for forming the composition of the present invention involves forming a pressure sensitive adhesive and mixing into it an antimicrobial treating solution comprising iodine, iodide, and a solvent. The resulting composition preferably contains N-vinyl-pyrrolidone (NVP) in the backbone of the pressure-sensitive adhesive which serves to complex iodine. It is believed that complexation provides stability while maintaining an appropriate equilibrium to provide sustained release of iodine.

The composition which is the resulting chemical complex of the aforementioned process is stable, nonirritating, non-sensitizing, non-toxic and non-traumatizing to skin or other tissues. Although it is generally recognized that an acid medium renders many broad-spectrum antimicrobial agents more stable, i.e. PVP-I, it was disclosed in U.S. Pat. No. 4,323,557 that a pressure-sensitive adhesive having a significant acidic content caused a negative alteration in the stability of iodine in the system disclosed therein. However, it has been found that inclusion of small amounts of acidic monomers does not appreciably affect the stability of the present adhesive system. Accordingly, additional monomers containing substituent groups which exhibit acid functionality, e.g., acrylic acid, methacrylic acid, itaconic acid, etc., may be copolymerized with the other components and used to form a useful adhesive of this invention.

It is believed that the iodine release is controlled by the copolymerization of low levels of the NVP into the adhesive backbone. The iodine release from the adhesive matrix is a function of the level of NVP copolymerized into the adhesive backbone. For a given iodine content, the higher the NVP level, the lower the antimicrobial activity. For this invention, the useful NVP comonomer level is less than 30% (preferentially 5–10%) of the total adhesive solids. At higher NVP levels, skin adhesion and antimicrobial activity are reduced.

An antimicrobial solution is used to incorporate iodine into the pressure-sensitive adhesive. This solution contains iodine (as used herein, iodine shall refer to $I_2$), inorganic iodide (e.g, potassium iodide) and a suitable solvent compatible with the adhesive and the iodine and iodide components. A solution recommended for use with the 5–10% NVP copolymer adhesive above would have a 0.5:1 to 4:1 molar ratio of iodide:iodine dissolved in acetone (preferred solution, 2:1 molar ratio of iodide-iodine). For example, a solution utilizing sodium iodide would have a formulation of 1–20 wt. % iodine, 1.2–24 wt.% sodium iodide and 97.8–56 wt.% acetone.

In particular, an IOA/NVP/Macromer: 88/9/3 adhesive (40% solids in ethyl acetate) to which has been added a solution containing 2% iodine and 2.4% sodium iodide in acetone to obtain an adhesive containing 2% iodine by weight of polymer solids is preferred. This adhesive is then coated onto a release liner at 6 grains per 24 sq. inches solids, dried and transfer coated onto a polyurethane film. Typical adhesion values are 70 grams per lineal inch width initially and 180 g/in. after 48 hrs.

Although the mechanism of complexation of iodine into the adhesive matrix of this invention is not completely understood, it is believed to have some analogy to the complexation of iodine with polyvinylpyrrolidone.

The skin adhesive compositions prepared in accordance with the present invention are easily coated upon suitable conformable backing materials by conventional coating techniques to produce skin adhesive coated sheet materials in accordance with the present invention. Suitable backings include any of the well-known backings which find use in medical or surgical fields. Typical examples of conformable backing materials which may be useful for the adhesive compositions of the present invention include those made of nonwoven fabric, woven fabric, knit, or medium to low tensile modulus synthetic films such as polypropylene, polyethylene, polyvinyl chloride, polyurethane, low modulus polyester, and ethyl cellulose. With respect to the conformable synthetic film backings, the film should have a tensile modulus of less than about 400,000 psi as measured in accordance with ASTM D-638 and D-882, preferably less than about 300,000 psi.

As noted above, backings may also be prepared of fabric such as woven fabric formed of threads of synthetic or natural materials such as cotton, nylon, or rayon, and the like or nonwoven fabric such as air laid webs of natural or synthetic fibers or blends of these. Preferred backings are those which permit transpiration of perspiration and/or tissue or wound exudate therethrough, e.g., nonwoven fabrics, woven fabrics, knits and the like.

Preferred backings are, accordingly, moisture vapor permeable in that they have a high rate of transmission of moisture vapor therethrough. These preferred backings have moisture vapor transmission values, when tested in accordance with ASTM E 96-80, of at least about 500 g/m$^2$, over 24 hours at 100° F. (38° C.) with a humidity differential of 80%, more preferably at least about 1000 g/m$^2$. For example, a continuous film backing prepared from a polyurethane sold under the tradename Estane, available from B. F. Goodrich, and a continuous film backing prepared from a polyester sold under the tradename Hytrel, available from DuPont, each have values of about 1000 to about 1500 g/$^2$ and woven backings such that those used for DURAPORE ® tape, available from 3M, have even higher values. In contrast, conventional polyethylene terephthalate films have approximate values of about 50 g/m$^2$.

The coated sheet materials may take the form of any article conventionally known to be utilized with skin adhesives such as tapes, patches, strips, wound dressings, monitoring or neuro-stimulating electrodes, drapes or the like. These articles may be dispensed from any convenient dispensing form, e.g., multi-layered pads, etc.

The skin adhesive compositions of the present invention may be coated by any of a variety of conventional coating techniques such as roll coating, spray coating, curtain coating, and the like. As is known to those skilled in the art, the particular method selected may depend upon the nature of the backing being employed. For example, where the backing is a nonwoven fabric, a suitable method for applying the adhesive copolymer thereto involves coating a solution of the adhesive copolymer in an organic solvent onto a release liner, followed by lamination of the nonwoven fabric backing to the (semi-dry) adhesive coating. The compositions may also be coated without modification by extrusion coating, coextrusion, hot-melt coating and the like by employing suitable conventional coating devices for this purpose. Primers may be used but they are not always necessary.

The skin adhesives of this invention may also be used in a method of adhering a substrate to skin. In this method an effective amount of a skin adhesive of this invention is interposed between the substrate and skin and pressure is applied to activate the skin adhesive. The substrate is preferably a sheet material as described above which is applied to the skin as a cover, patch or tape for the conventional purposes thereof.

CREEP COMPLIANCE TEST

In order to understand the advantages of this invention, it is necessary to understand how a fundamental rheological property of the pressure sensitive adhesives being used enables one to ascertain when and how the advantages of the invention are being obtained. The measurement of this property, which is the creep compliance of the PSA used to coat the tape backing, will be covered in detail later. The fundamentals of creep compliance as they relate to polymeric materials and, in particular, to viscoelastic polymers is covered in "Viscoelastic Properties of Polymers", John D. Ferry, 3rd Edition, John Wiley and Sons, 1980, Chapter 1. Also in "Treatise on Adhesion and Adhesives", Volume 2, "Materials", "Pressure Sensitive Adhesives", R. L. Patrick, Editor, Marcel Dekker, Inc., 1969. In "Properties and Structure of Polymers", Tobolsky, John Wiley and Sons, 1960, Chapter II, Section 6, the five regions of viscoelastic behavior are discussed. C. A. Dahlquist in "Handbook of Pressure Sensitive Adhesive Technology", edited by Donatas Satas, Van Nostrand Reinhold Company, 1982, Chapter 5 covers the entire stress-strain behavior of pressure sensitive adhesives and how this can be treated as a creep compliance phenomenon.

CREEP COMPLIANCE PROCEDURE

To measure the creep compliance of the skin adhesive of this invention, a 150-micrometer thickness of the skin adhesive is knife-coated onto a smooth film of polytetrofluoroethylene. The coated film is then dried to constant weight by placing the samples in an air-circulating oven generally for at least five minutes at 110° C. The skin adhesive, thus dried, is stripped from the polytetrafluoroethylene and two test pieces of equal area are die-cut and placed in the parallel plate creep compliane rheometer, one piece being on each side of the center plate, with an outer plate contacting the exposed surface of each. Screws which connect the two outer plates are then tightened so as to compress the interposed layers of skin adhesive approximately 10%. The parallel plates are placed in horizontal arrangement and one end of the center plate is connected to a linear variable transducer which measures the plate displacement (due to adhesive flow) and outputs an electrical signal, proportional to the displacement, to a chart recorder. A hook is attached to the opposite end of the center plate with a flexible wire extending horizontally from the hook and then downward over a pulley, the outer plates being held in a fixed position. A suitable weight (one which is sufficient to measurably deform the sample a distance no greater than its thickness) is attached to the free end of the wire, then the strip chart recorder is started. The weight typically used to exert the stress on the skin adhesive films of this invention is 500 grams. From the strip chart recorder, the time and the displacement (strain) are read and the applied force (stress) is recorded. The creep compliance at a given temperature is then calculated using the equation:

$$J_{(t)} = \frac{2A\,X}{hf}$$

where t is the time at which the measurement is taken, A is the area of one face of the adhesive samples, h is the thickness of the adhesive mass, X is the displacement at time t (where X is less than h) and f is the force due to the mass attached to the wire connected to the middle plate. Where A is expressed in $cm^2$, h in cm, X in cm, and f in dynes, then the compliance value $J_{(t)}$ is given in $cm^2/dyne$.

It has been found that the skin adhesive films of this invention have the required degree of compliance and the short term creep to function as an exceptionally fine pressure sensitive skin adhesive for medical and surgical applications, where the J value measured at ambient conditions at the end of a 3 minute period of subjection to stress is at least about $1.2 \times 10^{-5}$ $cm^2/dyne$ to about $2.3 \times 10^{-5}$ $cm^2/dyne$, preferably about $1.3 \times 10^{-5}$ $cm^2/dyne$ to about $2.0 \times 10^{-5}$ $cm^2/dyne$. It has been found that the higher the creep compliance, the greater the adhesive residue left on the skin after removal of the skin adhesive coated sheet material. Accordingly, creep compliance values greater than $2.3 \times 10^{-5}$ $cm^2/dyne$ are not preferred.

When the skin adhesive is to form a complex with iodine, e.g., a skin adhesive which has NVP as a B monomer, J values as low as $1.0 \times 10^{-5}$ $cm^2/dyne$ are acceptable. These J values are measured when the adhesive is substantially free of iodine, e.g, preferably less than about 0.1% by weight. This measurement is taken before treatment of the uncomplexed adhesive with the iodine/iodide solution or after the iodine has been volatilized from the complexed adhesive composition.

SKIN ADHESION TEST

The evaluation of the skin adhesives of this invention is highly subjective when the performance in contact with and upon removal from the human skin surface becomes part of the evaluation. For this reason a protocol was developed using a prescribed test panel of individuals who were selected to embrace the normal variations in skin surface that are encountered in medical practice. The result of this designed study enables one to get values which can be considered controlled and comparative. While these values are observational in respect to adhesive residue, sample lift and adhesion buildup, the procedures followed are in accord with carefully developed assessments of similar properties as described in detail in the Clinical Research Manual, Methodological Procedures for Adhesion Studies.

SKIN ADHESION PROCEDURE

The initial skin adhesion value ($T_o$) and the skin adhesion value after 24 or 48 hours in contact with the skin ($T_{24}$ or $T_{48}$) are essentially the widely accepted PSTC-1, peel adhesion test for single coated skin adhesive tapes measured at 180° angle. PSTC-1 is test method No. 1 of the Pressure Sensitive Tape Council, Glenview, Ill., Seventh Edition (1976); develped by the Specifications and Technical Committee of the Council. The test has been modified only to the extent that the tape is applied to the human skin surface on a selected area on the individual's back. Otherwise the steps in the procedure are as follows:

1. Tape samples 2.54 cm wide by 5.08 cm long are placed on the back of a human subject.
2. Each tape is rolled down with one forward and one reverse pass, using a 1-kilogram tape roller (described in Appendix B, Sections 2.7.1, 2.8.1 and 2.8.2 of Pressure Sensitive Tape Council) moved at the rate of about 30 cm per minute.
3. Adhesion to the skin is measured as the peel force required to remove the tape at 180° angle (PSTC-1).The peel force values are measured through the use of a strain-gauge mounted on a motor-driven carriage. The force of removal is reported in grams of adhesion per 2.54 cm of width of sample. The rate of removal is 15 cm per minute.
4. The adhesion to skin is measured immediately after initial application ($T_o$) and after 24 or 48 hours of continuous contact with the skin ($T_{24}$ or $T_{48}$).

Preferred skin adhesive will generally exhibit a $T_o$ of between 50 grams to about 100 grams and a $T_{48}$ of between about 150 grams to about 300 grams.

ADHESIVE RESIDUE TEST

When the skin adhesion test described above is performed, the skin underlying the tape sample is visually inspected to determine the amount of adhesive residue left on the surface of the skin. Each sample is assigned a numerical rating from 0 to 5 based on the following scale.

| Rating | Definition |
|---|---|
| 0 | No visible residue; |
| 1 | Only residue at edges of tape; |
| 2 | Residue covering 1% to 25% of tested area; |

-continued

| Rating | Definition |
|---|---|
| 3 | Residue covering 25% to 50% of tested area; |
| 4 | Residue covering 50% to 75% of tested area; |
| 5 | Residue covering 75% to 100% of tested area. |

The results of all tape samples of a given panel were averaged and are reported below. Due to the subjectivity of the visual inspection for residue, no degree of precision should be inferred from the numbers to the right of the decimal point and those numbers should be treated as only rough approximations.

Preferred skin adhesives will generally exhibit an average rating below about 2.5.

EXAMPLES

In the following examples, an arabic numeral denotes an example of a copolymer contemplated as a skin adhesive of this invention, a capital letter denotes a comparative example and the denotation "M-X", wherein X is an arabic numeral, denotes a macromer useful in preparing the skin adhesives of this invention.

PREPARATION OF MACROMER

The "C" moiety of the general formula A-B-C is a polymeric material which has a copolymerizable vinyl group which copolymerizes with monomers A and B under polymerizing conditions. The C moiety, while being polymeric in one sense, actually behaves as a monomer and is referred to in the literature as a macromolecular monomer which is shortened to the term "macromer" for convenience. For the purpose of this invention, representative preparations of the macromers that are used follows.

EXAMPLE M-1

This methacrylate-terminated styrene macromer having an average molecular weight of about 9000 was prepared using a five-liter four-necked flask, fitted with a thermometer, mechanical stirrer, septum, Dean-Stark trap and condenser. 150 grams (1.44 moles) of styrene were charged into the flask which contained 1155 grams cyclohexane, resulting in an 11.5% by weight solution. The solution was heated to about 50° C. and a 1.4 molar solution of sec-butyl lithium in cyclohexane was added dropwise until a faint yellow color persisted, then 10.7 ml of additional sec-butyl lithium cyclohexane solution was added rapidly. The reaction mixture was maintained at 65° C. by cooling. After about one hour, the solution was allowed to cool to 35° C. and then ethylene oxide gas was introduced over the reaction mixture which was agitated rapidly for 15 minutes until the orange color of polystyryl lithium had disappeared. The reaction was then quenched with 5 ml (51.2 meq.) of methacryloyl chloride. The polymer solution was reduced in volume and the polymer was precipitated and dried. Gel permeation chromatography revealed a number average molecular weight of 8394, weight average molecular weight of 8842 and polydispersity of 1.05.

EXAMPLE M-2

An acrylate-terminated polymethyl methacrylate polymeric monomer having an average molecular weight of 10,000 was prepared. Recrystallized dried fluorene, five parts, was placed in a 1,000 ml three-necked flask fitted with stirrer, thermometer, argon inlet and rubber septum, all of which had been previously flamed under argon. Dried tetrahydrofuran, 400 parts, was distilled into the flask and 15 parts of a 1.4N solution of sec-butyllithium in cyclohexane were added through the septum, producing an orange-red solution of "fluorenyl lithium" under slight argon pressure. The flask contents were cooled to −76° C. and 65 parts dried, freshly distilled methyl methacrylate (MMA) were rapidly added through the septum. The reaction temperature quickly rose to −20° C. and then was gradually returned to −76° C. by cooling. After one hour of stirring, 3 parts of ethylene oxide were bubbled into the flask and the flask was warmed to −10° C., causing the liquid to change from orange-red to light yellow. Acryloyl chloride (3 parts) was then added to quench. The reaction mixture was then warmed to room temperature and added dropwise with vigorous stirring to 4 liters of hexane, causing a white solid to precipitate. The solid was filtered, dried, redissolved in toluene, filtered to remove impurities and precipitated in methanol. The resulting white solid was a polymeric monomer having the following properties: weight average molecular weight 10,420 and polydispersity 2.6.

In addition to the above macromers the following macromers prepared by means similar to those used above, were used to prepare the skin adhesives shown in the following examples:

Example M-3: a methacrylate-terminated polystyrene macromer having a weight average molecular weight of about 10,000 g/mol.

Example M-4: a methacrylate-terminated polystyrene macromer having a weight average molecular weight of about 13,000 g/mol.

Example M-5: a methacrylate-terminated poly(methyl methacrylate) macromer having a weight average molecular weight of about 13,000 g/mol.

Preparation of Skin Adhesive

EXAMPLE 1

This is a representative preparation of the skin adhesives which are comprised of the A-B-C moieties of the general formula of this invention.

The copolymerization reaction takes place in a sealed, one-quart amber bottle which has been purged by bubbling nitrogen through the solution at a flow rate of one liter per minute for two minutes after which the bottle is sealed. The solution through which the nitrogen has been bubbled is comprised of 190 grams of isooctyl acrylate monomer (IOA), 4 grams of acrylic acid (AA), 4 grams of 2-polystyrylethyl methacrylate macromer (commercially available as CHEMLINK ® 4500, 13,000 M.W. from Sartomer Chemical Company), 300 grams of ethyl acetate (A.R. grade), 0.6 gram 2,2'-azobisisobutyronitrile (commercially available from DuPont as VAZO ® 64), plus 2.5 gram of a 1% solution of carbon tetrabromide in isooctyl acrylate which results in a CBr$_4$ charge of 0.012%. The bottle thus charged is tumbled for 24 hours in a waer bath at 55° C. to effect essentially complete polymerization. The yield for this charge was a solution containing 38.65% of copolymer comprised of 96% isooctyl acrylate/2% acrylic acid/2% 2-polystyrylethyl methacrylate macromer. The inherent viscosity of this adhesive polymer measured in dilute solution of ethyl acetate was 0.904.

The Brookfield viscosity measurement was 6,000 centipoise.

The following tables, Tables 1, 2 and 3, set forth the composition, inherent viscosity and creep compliance values of copolymers prepared in a manner similar to that of Example 1. The abbreviations ACM, MA and NVP were used for acrylamide, methacrylic acid and N-vinylpyrrolidone, respectively.

TABLE 1

Skin Adhesives from Acrylic Acid Copolymers

| Ex. No. | IOA (pbw) | AA (pbw) | Macromer (pbw(identity)) | IV | J ($\times 10^{-5}$ cm$^2$/dyne) |
|---|---|---|---|---|---|
| 1 | 96 | 2 | 2(M-4) | 0.90 | 1.98 |
| 2 | 96 | 2 | 2(M-4) | 0.80 | 2.49 |
| 3 | 96 | 2 | 2(M-4) | 0.74 | 2.80 |
| 4 | 96 | 2 | 2(M-4) | 0.67 | 3.70 |
| 5 | 96 | 2 | 2(M-4) | 0.93 | 1.80 |
| 6 | 95 | 2 | 3(M-4) | 0.81 | 1.79 |
| 7 | 95 | 2.5 | 2.5(M-4) | 0.80 | 1.73 |
| 8 | 96 | 1 | 3(M-4) | 0.78 | 2.25 |
| 9 | 95 | 2 | 3(M-4) | 0.72 | 2.45 |
| 10 | 95 | 2.5 | 2.5(M-4) | 0.71 | 2.41 |
| 11 | 96 | 1 | 3(M-4) | 0.69 | 2.90 |
| 12 | 96 | 2 | 2(M-4) | 0.91 | 1.85 |
| 13 | 96 | 2 | 2(M-3) | 0.89 | 1.72 |
| 14 | 96 | 2 | 2(M-3) | 0.94 | 1.46 |
| 15 | 98 | 1 | 1(M-3) | 0.78 | 3.36 |
| 16 | 96 | 1 | 3(M-3) | 0.83 | 1.59 |
| 17 | 96 | 1 | 3(M-3) | 0.75 | 1.59 |
| 18 | 94 | 3 | 3(M-3) | 0.78 | 1.31 |
| 19 | 98 | 1 | 1(M-3) | 0.57 | 12.70 |
| 20 | 96 | 1 | 3(M-3) | 0.60 | 5.21 |
| 21 | 96 | 3 | 1(M-3) | 0.55 | 3.36 |
| 22 | 94 | 3 | 3(M-3) | 0.58 | 2.18 |
| 23 | 96 | 2 | 2(M-3) | 0.65 | 3.60 |
| 24 | 98 | 1 | 1(M-3) | 0.89 | 2.77 |
| 25 | 97 | 1.5 | 1.5(M-3) | 0.86 | 1.98 |
| 26 | 97 | 0 | 3(M-3) | 0.80 | 1.71 |
| 27 | 96 | 3 | 1(M-3) | 0.90 | 1.71 |
| 28 | 96 | 2 | 2(M-3) | 0.87 | 1.65 |
| 29 | 96 | 1 | 3(M-3) | 0.83 | 1.38 |
| 30 | 95 | 2.5 | 2.5(M-3) | 0.87 | 1.24 |
| 31 | 95 | 0 | 5(M-3) | 0.83 | 0.96 |
| 32 | 96 | 2 | 2(M-5) | 0.82 | 2.99 |
| 33 | 80 | 0 | 20(M-5) | 0.76 | 0.23 |

TABLE 2

Skin Adhesives from Acrylamide Copolymers

| Ex. No. | IOA (pbw) | ACM (pbw) | Macromer (pbw(identity)) | IV | J ($\times 10^{-5}$ cm$^2$/dyne) |
|---|---|---|---|---|---|
| 34 | 90 | 4 | 6(M-1) | 0.58 | 0.39 |
| 35 | 97 | 2 | 1(M-3) | 0.86 | 3.25 |
| 36 | 95 | 2 | 3(M-3) | 0.82 | 2.20 |
| 37 | 95 | 4 | 1(M-3) | 0.92 | 1.15 |
| 38 | 93 | 4 | 3(M-3) | 0.87 | 0.94 |
| 39 | 97 | 2 | 1(M-3) | 0.53 | 8.57 |
| 40 | 95 | 2 | 3(M-3) | 0.53 | 3.48 |
| 41 | 95 | 4 | 1(M-3) | 0.58 | 1.62 |
| 42 | 93 | 4 | 3(M-3) | 0.60 | 1.20 |
| 43 | 95 | 3 | 2(M-3) | 0.67 | 2.04 |
| 44 | 98 | 1.5 | 0.5(M-3) | 1.03 | 1.98 |
| 45 | 98 | 0.5 | 1.5(M-3) | 0.94 | 2.08 |
| 46 | 97 | 2 | 1(M-3) | 1.05 | 1.20 |
| 47 | 97 | 1 | 2(M-3) | 0.95 | 1.41 |
| 48 | 96 | 3 | 1(M-3) | 1.10 | 0.87 |
| 49 | 96 | 2 | 2(M-3) | 1.06 | 1.04 |
| 50 | 96 | 1 | 3(M-3) | 0.98 | 1.22 |
| 51 | 94 | 2.5 | 3.5(M-3) | 1.09 | 0.81 |
| 52 | 95 | 0 | 5(M-3) | 0.90 | 0.88 |
| 53 | 97 | 2 | 1(M-5) | 0.95 | 2.27 |

TABLE 3

Skin Adhesives from N—vinylpyrrolidone Copolymers

| Ex. No. | IOA (pbw) | NVP (pbw) | Macromer (pbw(identity)) | IV | J ($\times 10^{-5}$ cm$^2$/dyne) |
|---|---|---|---|---|---|
| 54 | 93 | 5 | 2(M-3) | 1.04 | 1.60 |
| 55 | 91 | 6 | 3(M-3) | 1.05 | 1.06 |
| 56 | 89 | 7 | 4(M-3) | 1.09 | 0.86 |
| 57 | 89 | 5 | 6(M-3) | 0.99 | 0.69 |
| 58 | 88 | 10 | 2(M-3) | 1.20 | 1.11 |
| 59 | 87 | 8 | 5(M-3) | 1.14 | 0.70 |
| 60 | 86 | 10 | 4(M-3) | 1.19 | 0.79 |
| 61 | 85 | 12 | 3(M-3) | 1.28 | 0.76 |
| 62 | 84 | 14 | 2(M-3) | 1.36 | 0.78 |
| 63 | 84 | 10 | 6(M-3) | 1.26 | 0.58 |
| 64 | 84 | 14 | 2(M-5) | 0.92 | 1.23 |
| 65 | 87 | 10 | 3(M-5) | 0.83 | 1.66 |

The following Skin Adhesion Tests from four separate testing panels illustrate the general rule that copolymers having creep compliance values within the range of 1.2 to 2.3×10$^{-5}$ cm$^2$/dyne give adhesive tapes having higher initial adhesion without objectionable adhesion build over time. The tapes were comprised of the adhesives shown on a woven backing such as that of DURAPORE ® available from 3M, St. Paul, MN. The control is a copolymer of isooctyl acrylate and acrylic acid, 95.5 and 4.5 parts by weight respectively, having the IV and J values shown commercially available as DURAPORE ® tape from 3M.

TABLE 4

Skin Adhesion Tests

| Ex. No. | Copolymer | IV | J | Skin Adhesion $T_0$ | Skin Adhesion $T_{48}$ | Residue Rating |
|---|---|---|---|---|---|---|
| | Panel 1 | | | | | |
| 66 | IOA/AA/M-3:96/2/2 | 0.94 | 1.46 | 76 | 157 | 1.17 |
| 67 | IOA/AA/M-3:96/2/2 | 0.84 | 1.65 | 85 | 190 | 1.11 |
| 68 | IOA/ACM/M-3:97/2/1 | 0.83 | 2.15 | 225 | 471 | 2.89 |
| 69 | IOA/NVP/M-3:87/10/3 | 0.93 | 1.61 | 102 | 268 | 2.17 |
| 70 | IOA/NVP/M-3:84/14/2 | 0.91 | 1.74 | 291 | 388 | 2.44 |
| A | Control | 1.55 | 0.84 | 67 | 234 | 1.78 |
| | Panel 2 | | | | | |
| 71 | IOA/AA/M-3:96/2/2 | 0.89 | 1.72 | 69 | 270 | 0.67 |
| 72 | IOA/NVP/M-3:87/10/3 | 1.33 | 1.09 | 91 | 366 | 0.78 |
| 73 | IOA/ACM/M-3:97/2/1 | 1.10 | 1.39 | 106 | 499 | 1.61 |
| B | Control | 1.55 | 0.84 | 38 | 242 | 0.72 |
| | Panel 3 | | | | | |
| 74 | IOA/AA/M-3:96/2/2 | 0.93 | 1.80 | 79 | 128 | 1.00 |
| 75 | IOA/AA/M-3:96/2/2 | 0.93 | 1.80 | 76 | 127 | 0.88 |
| C | Control | 1.55 | 0.84 | 60 | 317 | 2.39 |
| | Panel 4 | | | | | |

TABLE 4-continued

| | | Skin Adhesion Tests | | | | |
|---|---|---|---|---|---|---|
| | | | | Skin Adhesion | | Residue |
| Ex. No. | Copolymer | IV | J | T₀ | T₄₈ | Rating |
| 76 | IOA/AA/M-3:96/2/2 | 0.93 | 1.80 | 56 | 228 | 0.78 |
| D | Control | 1.55 | 0.84 | 36 | 256 | 1.11 |
| | Panel 5 | | | | | |
| 77 | IOA/AA/M-3:96/2/2 | 0.94 | 1.46 | 53 | 219 | 1.22 |
| E | Control | 1.55 | 0.84 | 30 | 216 | 1.00 |

The adhesives of U.S. Pat. No. 4,554,324, having a shear strength value below 50 minutes were tested for their utility as skin adhesives by testing their creep compliance. (The high shear strengths of the adhesives having shear strengths above 50 minutes will prevent these adhesives from creep compliance values low enough to act as a skin adhesive.) The results of these tests are shown in Table 5, below:

TABLE 5

| | | Adhesives Disclosed in U.S. Ser. No. 419,025 | | | | |
|---|---|---|---|---|---|---|
| Ex. No. | Ser. No. 419,025 Ex. No. | IOA (pbw) | B Monomer (pbw) | Macromer (see Ser. No. 419,025 for composition) | I.V. | J ($\times 10^{-5}$ cm²/dyne) |
| 73 | 41 | 89.3 | AA/4.7 | 6 | .60 | 1.58 |
| 74 | 43 | 88 | None | 12 | .57 | 1.24 |
| E | 67 | 80 | None | 20 | .76 | .23 |
| F | 59 | 90 | ACM/4 | 6 | .58 | .39 |
| G | 55 | 90 | MA/4 | 6 | .73 | .76 |
| H | 3 | 90.5 | AA/6.5 | 3 | .70 | 1.05 |
| I | 66 | 88 | AA/6 | 6 | .28 | 3.13 |

It can be seen from the above table that out of the many adhesives disclosed in U.S. Pat. No. 4,554,324, only two have the creep compliance required to act as skin adhesives in accordance with this invention and only one within the preferred range of creep compliance.

EXAMPLES 75–86

The IV and compliance (J) values were taken by measurements on the adhesive without the Iodine/NaI. A solution of 2% iodine and 2.4%NaI (by weight) in acetone was added to each adhesive to achieve an overall composition of 2% iodine and 2.4% NaI by weight of adhesive solids. The adhesives were coated onto a silicone liner, dried to evaporate the solvents, and laminated to a polyurethane backing so as to achieve a dried coating weight of approximately 25.1 g/m². The skin adhesion procedure described above was then followed to obtain the results shown in Table 6 below.

TABLE 6

| Sample | IOA/NVP/M-3 Adhesive Terpolymer | IV | J | Skin Adhesion T0 | T48 | Residue |
|---|---|---|---|---|---|---|
| 75 | 92/6/2 | 1.04 | 2.11 | 88 | 222 | 2.0 |
| 76 | 91/6/3 | 1.20 | 1.25 | 75 | 137 | 2.2 |
| 77 | 90.5/7.5/2 | 1.24 | 1.29 | 75 | 212 | 1.7 |
| 78 | 90/7/3 | 1.08 | 1.36 | 71 | 159 | 1.9 |
| 79 | 90/6/4 | 1.20 | .99 | 58 | 124 | 1.8 |
| 80 | 89.5/8.5/2 | 1.29 | 1.11 | 69 | 183 | 1.9 |
| 81 | 89/8/3 | 1.28 | .94 | 69 | 154 | 1.2 |
| 82 | 88.5/9.5/2 | 1.18 | 1.29 | 80 | 230 | 2.0 |
| 83 | 88.5/7.5/4 | 1.28 | .92 | 54 | 104 | 1.5 |
| 84 | 88/9/3 | 1.14 | 1.06 | 72 | 159 | 1.8 |
| 85 | 87/11/2 | 1.21 | 1.14 | 81 | 190 | 1.5 |
| 86 | 87/9/4 | 1.15 | .91 | 60 | 167 | 1.8 |

What is claimed is:

1. A method of adhering a substrate to skin comprising the step of interposing between the substrate and the skin an adhesive composition comprising a copolymer of copolymerized A monomers, C macromers, and optionally B monomers, wherein:

A is a monomeric acrylate or methacrylate ester of a non-tertiary alcohol, said alcohol having from about 1 to about 14 carbon atoms with the average number of carbon atoms being from about 4 to about 12;

B, when used, is at least one ethylenically unsaturated compond copolymerizable with said A monomer, with B monomers comprising from about 0% to about 25% of the total weight of A and B monomers; and C is a macromer having the general formula:

$$X-(Y)_n-Z$$

wherein:

X is a vinyl group copolymerizable with said A and B monomers, X having the general formula:

wherein
R is a hydrogen atom or a COOH group and R' is a hydrogen atom or a methyl group;
Y is a divalent linking group with n being either 0 or 1; and
z is a monovalent polymeric moiety having a $T_g$ greater than about 20° C. and a molecular weight in the range of about 2,000 to about 30,000 and being essentially unreactive under copolymerization conditions, Z having the general formula:

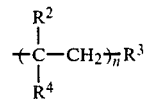

wherein R² is a hydrogen atom or a lower alkyl group, R³ is a lower alkyl group, n is an integer from about 20 to about 500, and $R^4$ is a monovalent radical selected from the group consisting of:

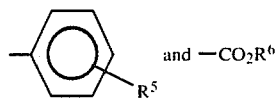

wherein $R^5$ is a hydrogen atom or a lower alkyl group and $R^6$ is a lower alkyl group;

wherein the number and composition of said C macromers is such that the adhesive composition has a creep compliance of at least about $1.2 \times 10^{-5}$ cm$^2$/dyne when measured after about 3 minutes of subjection to stress.

2. A method as defined in claim 1 wherein said copolymer contains from about 1% to about 7% by weight of C macromer.

3. A method as defined in claim 1 wherein said copolymer has an inherent viscosity of about 0.5 to about 1.4.

4. A method as defined in claim 1 wherein the substrate comprises a skin conformable backing member having a water vapor permeability of at least about 500 g/m$^2$ when measured over about 24 hours at a temperature of about 100° F. under a humidity differential of about 80%.

5. A method as defined in claim 1 wherein the substrate comprises a skin conformable backing member having conformability which is at least equivalent to that of a film having a tensile modulus of less than about 400,000 psi.

6. A method as defined in claim 1 wherein said B monomer is selected from the group consisting of acrylic acid, methacrylic acid, itaconic acid, acrylamide, methacrylamide, acrylonitrile, methacrylonitrile, vinyl acetate and N-vinylpyrrolidone.

7. A method as defined in claim 1 wherein said A monomer is isooctyl acrylate, said B monomer is present and is acrylic acid, and said C macromer is methacrylate-terminated polystyrene.

8. A method as defined in claim 7 wherein said copolymer contains from about 1% to about 7% by weight of C macromer and from about 1% to about 4% by weight of B monomer.

9. A method as defined in claim 1 wherein said copolymer contains from about 1% to about 4% by weight of acrylic acid as the B monomer.

10. A method as defined in claim 1 wherein said copolymer contains from about 1% to about 4% by weight of acrylamide as the B monomer.

11. A method as defined in claim 1 wherein said B monomer is present and is N-vinylpyrrolidone.

12. A method as defined in claim 11 wherein said copolymer contains from about 5% to about 15% by weight of N-vinylpyrrolidone as the B monomer.

13. A method as defined in claim 11 wherein said copolymer is complexed with iodine.

14. A method as defined in claim 13 wherein the amount of iodine in said copolymer complex is from about 1% to about 3% by weight of the copolymer.

15. A method as defined in claim 1 wherein said A monomer is isooctyl acrylate, said B monomer is present and is N-vinylpyrrolidone, and said C monomer is methacrylate-terminated polystyrene.

16. A method as defined in claim 1 wherein N-vinylpyrrolidone and an acidic monomer selected from the group consisting of acrylic acid, methacrylic acid, and itaconic acid are both included in the copolymer as B monomers.

17. A method as defined in claim 1 wherein said substrate is made from a synthetic film.

18. A method as defined in claim 1 wherein said substrate is made from a conformable fabric.

19. A method as defined in claim 1 wherein the number and composition of said C macromers is such that the adhesive composition has a creep compliance of between about $1.2 \times 10^{-5}$ cm$^2$/dyne and about $2.3 \times 10^{-5}$ cm$^2$/dyne when measured after about 3 minutes of subjection to stress.

* * * * *

UNITED STATES PATENT AND TRADEMARK OFFICE
CERTIFICATE OF CORRECTION

PATENT NO. : 4,693,776

DATED : September 15, 1987                           Page 1 of 2

INVENTOR(S) : Krampe, et al.

It is certified that error appears in the above-identified patent and that said Letters Patent is hereby corrected as shown below:

Col. 2, line 8, please insert "this divisional application issued on November 19, 1985 as U.S. Patent No. 4,554,324." after the semi-colon.

Col. 2, line 37, please insert a left parenthesis before "U.S."

Col. 3, line 37, "x" should read --X--.

Col. 3, line 65, "porperties" should read --properties--.

Col. 5, line 20, please insert --#-- before "50".

Col. 7, line 23, please delete left parenthesis.

Col. 7, line 25, please delete right parenthesis.

Col. 8, line 27, "reacion" should read --reaction--.

Col. 9, line 11, "psa" should read --PSA--.

Col. 12, line 7, "g/$^2$" should read --g/m$^2$--.

Col. 12, line 55, "viscoeleastic" should read --viscoelastic--.

UNITED STATES PATENT AND TRADEMARK OFFICE
CERTIFICATE OF CORRECTION

PATENT NO. : 4,693,776
DATED : September 15, 1987
INVENTOR(S) : Krampe, et al

Page 2 of 2

It is certified that error appears in the above-identified patent and that said Letters Patent is hereby corrected as shown below:

Col. 13, line 11, "compliane" should read --compliance--.
Col. 14, line 28, "develped" should read --developed--.

Signed and Sealed this

Fifteenth Day of March, 1988

Attest:

DONALD J. QUIGG

*Attesting Officer*      *Commissioner of Patents and Trademarks*